United States Patent [19]
Waddell et al.

[11] 3,965,909
[45] June 29, 1976

[54] ANGIOGRAPHIC CATHETER AND METHOD OF MANUFACTURE

[75] Inventors: Seid W. Waddell, Tarentum; Marlin S. Heilman, Gibsonia, both of Pa.

[73] Assignee: Medrad, Inc., Pittsburgh, Pa.

[22] Filed: Apr. 22, 1975

[21] Appl. No.: 570,998

[52] U.S. Cl. .............................. 128/348; 128/345
[51] Int. Cl.² .................................... A61M 25/00
[58] Field of Search ............ 128/344, 345, 347, 356

[56] References Cited
UNITED STATES PATENTS

| | | | |
|---|---|---|---|
| 3,023,461 | 3/1962 | Sherman | 264/98 |
| 3,434,869 | 3/1969 | Davidson | 128/349 |
| 3,485,234 | 12/1969 | Stevens | 128/2 |
| 3,498,286 | 3/1970 | Polanyi | 128/2 |
| 3,566,874 | 3/1971 | Shepard et al. | 128/349 |
| 3,618,614 | 10/1972 | Flynn | 60/297 |
| 3,635,223 | 1/1972 | Kieman | 128/348 |
| 3,695,921 | 10/1972 | Sheperd et al. | 427/2 |
| 3,695,921 | 10/1972 | Shepard et al. | 128/348 |
| 3,721,231 | 3/1973 | Hubert | 128/2.05 |
| 3,819,792 | 6/1974 | Ono et al. | 264/95 |
| 3,865,666 | 2/1975 | Shoney | 156/245 |

*Primary Examiner*—Louis G. Mancene
*Assistant Examiner*—Robert F. Cutting
*Attorney, Agent, or Firm*—Fleit & Jacobson

[57] ABSTRACT

There is disclosed a multiwall catheter and a method for the manufacture thereof. The catheter comprises two co-extensive elongated continuous plastic tubes having an intermediate braid sheath extending to within a few inches of the composite tube end where the composite tubing is formed by a modified pultrusion process. The first tube is preformed, encased in a non-metallic braid and pulled through a heated die to form a composite tube. The composite tube is then encased in a second preformed tube and the assembly is pulled through a second heated die to form the multiwall catheter. Multiple mechanical advantages for catheter rotation are provided by three varying diameters on the proximal end of the catheter. Also, the technique of making the outside surface of the catheter of a microporous plastic material to act as an anticoagulant reservoir is described.

29 Claims, 10 Drawing Figures

ANGIOGRAPHIC CATHETER AND METHOD OF MANUFACTURE

BACKGROUND OF THE INVENTION

The present invention relates to catheters and more particularly to multiwall catheters made by a modified pultrusion process.

Current surgical techniques, such as in angiography, often require the use of a catheter which is inserted into a lumen of a vein or other blood vessel. Fluid is injected through the catheter, often at very high pressures, and serves as a contrast media for use in conjunction with diagnostic x-ray equipment.

Because these catheters are used inside a patient's body, they are subject to many strict, and yet conflicting requirements. For example, the catheter must be capable of negotiating a precise path within the patient's body, having the ability to change direction to enter any desired portion of the vascular system. Naturally, therefore, the catheter must be flexible enough to easily move through a blood vessel, and yet without undergoing permanent deformation. Also, the catheter must be stiff enough to be easily guided and controlled by a physician. The catheter physical characteristics are also subject to several strict, yet opposing requirements. For example, the outer diameter of the catheter must be kept small to fit through a minimum-size hole in an artery or vein, yet the inner diameter must be large enough to accommodate the desired fluid flow rates. In addition, the fluid flows frequently developed in angiography generate high pressures inside the catheter, and hence the catheter walls must be strong enough to resist bursting forces.

As even the smallest catheter will come into contact with the body, the catheter surface characteristics are also important. The catheter outer surface must be smooth and uniform to reduce friction and formation of blood clots (thrombosis). While various of the presently known catheters meet some of the above-mentioned conflicting requirements, no known catheter can boast of meeting all.

One approach to a blood clot resistant catheter surface has been to chemically bond an anticoagulant material to the catheter surface. The present invention offers a novel alternative to a chemically bonded anticoagulant.

One type of catheter which has proven effective is the multiwall catheter, formed by a plurality of coextensive tubes. These catheters are generally manufactured by co-extruding two or more types of plastic tubes, frequently with a braid sheath of metal between the plastic tubes and serves to provide torsional rigidity while preserving longitudinal flexibility.

These known catheters have not been entirely successful because the metal braid is susceptible to kinking and permanent deformation. Such permanent deformation may result in catheter failure at the location of the kink. The wall thickness of several presently known extruded multiwall catheters has extra thickness to shield the stainless steel wire braid. Accordingly, contrast media flow has been compromised for a given catheter size.

Most presently known multiwall catheters are not inherently continuous, but instead have a tip portion welded to a body portion. In order that these known catheters may be guided by the physician and yet be capable of following a blood vessel, they are developed from a flexible distal tip welded to a more firm body portion. With such a construction there is always the possibility of the distal tip separating from the catheter thereby presenting serious problems.

SUMMARY OF THE INVENTION

The present invention overcomes the drawbacks noted above by providing an improved multiwall catheter having high torsional rigidity for guiding purposes, flexibility throughout its entire length, especially its distal end, a smooth uniform outer surface, high resistance to bursting, excellent control over wall thickness, and absence of metallic wire in the catheter wall. The catheter is produced by a pultrusion process wherein an elongated tube is pulled through a heated die which produces a smooth uniform catheter, as opposed to an extrusion process wherein a tube is formed by molten plastic being pushed through a die. The pultrusion process can be closely controlled to produce a catheter having precise and uniform dimensions and characteristics. A non-metallic intermediate braid allows catheter flexing while providing the torsional rigidity necessary for guiding the catheter tip into the vessel of interest, and the braid is discontinued at the distal end to give the distal end maximum flexibility. A microporous outer catheter wall surface is described which may act as a reservoir for an anticoagulant.

Briefly, the present invention relates to an improved multiwall catheter and the manufacture thereof. A non-metallic braid sheath is positioned between two co-extensive, continuous elongated plastic tubes. The braid sheath is isolated from the catheter flow path by the inner tube and from sensitive body surfaces by the outer tube. The strict dimensions and surface uniformity requirements are satisfied by manufacturing the catheter using a pultrusion process. The braid sheath is integrated into the inner tube, and the composite structure is integrated into the outer tube in two separate successive pultruding steps. The pultrusion process produces a catheter having a smooth uniform outer surface and closely controlled dimensions. The inner and outer tubes are continuous, with the distal tip being integral with the catheter body, and hence the tip is resistant to separation from the catheter body. The intermediate non-metallic braid enables the catheter to meet the conflicting requirements of torsional rigidity and longitudinal flexibility. The braided sheath also provides support for the catheter so a thin walled catheter can adequately enjoy high burst resistance and minimum size.

It is accordingly a broad object of the present invention to provide a catheter having a smooth uniform outer surface.

Another object of the present invention is to provide a catheter capable of reliably withstanding high internal pressures.

A further object of the present invention is to provide a catheter which is flexible, yet stiff enough to be easily controlled during insertion procedures.

Still another object of the present invention is to provide a continuous catheter having a distal tip which is more flexible than its body.

Yet another object of the present invention is to provide a catheter which will resist permanent deformation during insertion and removal thereof.

Still another object of the present invention is to provide a catheter capable of establishing maximum flow rate for a minimum size outside diameter.

A further object of the present invention is to provide a small diameter radiopaque angiographic catheter which is capable of undergoing high-pressure injections, and which develops minimum trauma at the patient's vascular point of catheter entry.

An additional object of the present invention is to provide an angiographic catheter which may readily and safely be guided through the vascular system of a patient.

A further object of the present invention is to provide a softer catheter surface that is resistant to thrombosis by virtue of continuous leaching of an anticoagulant material.

BRIEF DESCRIPTION OF THE DRAWINGS

These and other objects of the present invention, as well as many of the attendant advantages thereof, will become more readily apparent when referencce is made to the following description taken in conjunction with the accompanying drawings.

DETAILED DESCRIPTION OF THE DRAWINGS

Figure 1:
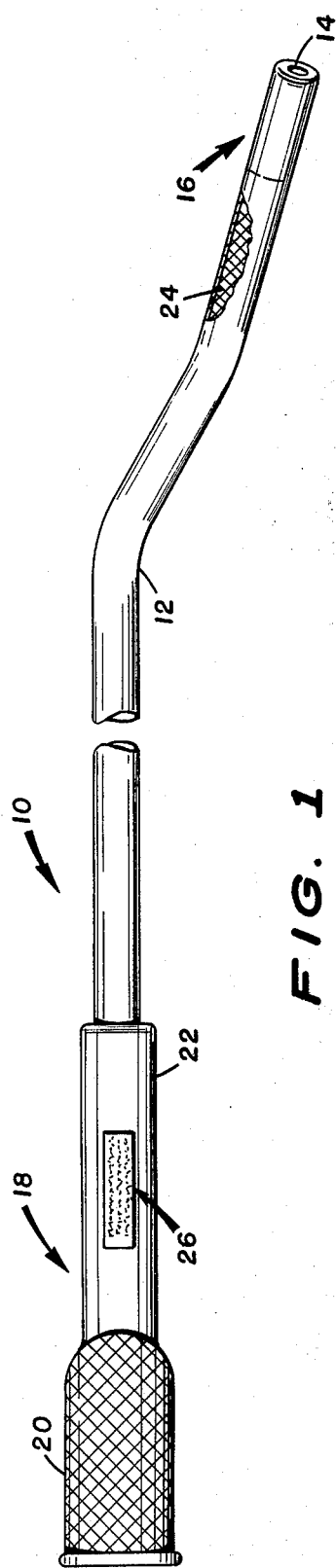
FIG. 1 is a perspective view illustrating a catheter constructed in accordance with the teachings of the present invention.

With reference first to FIG. 1, the overall construction of the inventive catheter will be described. The catheter is shown generally at 10 and comprises an elongated flexible main body 12 having a central passage or lumen 14 extending entirely therethrough. The catheter 10 has a distal tip 16 and a proximal end 18 at the respective ends of the main body 12. The extreme proximal end of the catheter 10 is attached to a knurled finger control mechanism 20 and supported by means of a shrink tube 22. The finger control mechanism 20 is held and manipulated by the physician; and the shrink tube 22 is employed to contain information such as catheter size and length, as illustrated at 26, as well as providing a second finger control diameter for catheter rotation. The main body 12 of the catheter 10 is of a thermoplastic material, and is reinforced throughout substantially its entire length by means of an embedded non-metallic braid 24 extending from the proximal end to several inches from the distal tip.

As noted above, the catheter of the present invention is manufactured by what may be termed a modified pultrusion process. The non-metallic braid 24 is embedded in and made integral with a thermoplastic tube which is itself developed from two preformed thermoplastic tubes bonded together by being pulled through heated dies. With references to FIGS. 2 through 8, the inventive manufacturing process will be described.

Figure 3:
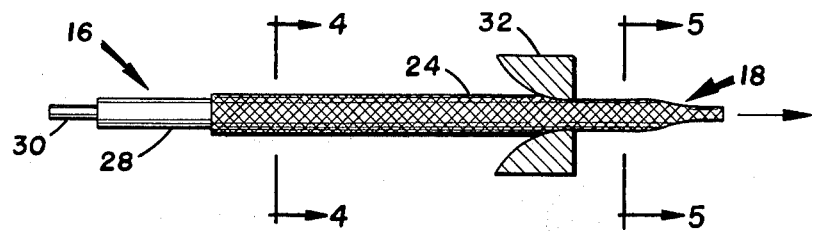
FIG. 3 is an illustration representing an early step in the inventive manufacturing procedure.
Figure 4:
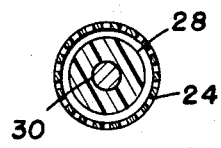
FIG. 4 is a cross section taken along line 4—4 of FIG. 3.
Figure 5:
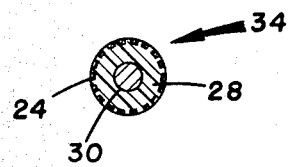
FIG. 5 is a cross section taken along line 5—5 of FIG. 3.

The first step of the inventive process is to cover a preformed thermoplastic tube with a non-metallic braid which has been woven of fiber that has previously been saturated with a compatible thermoplastic material. This step is illustrated in FIGS. 3 and 4 wherein the thermoplastic tube is shown at 28, and the non-metallic braid at 24. A solid mandrel 30 is introduced into the lumen 14 of the tube 28 to prevent deformation of the lumen during the later stages of the pultrusion process.

The proximal end 18 of the tube 28 is covered by the braid, and defines a site where the pulling apparatus associates. This end is then grasped and pulled through a heated die shown generally at 32 in FIG. 3. Such step results in the fabrication of a composite assembly such as that shown at 34 in FIG. 5. In this condition, the non-metallic braid 24 has become embedded into the surface of the thermoplastic tube 28.

Figure 2:
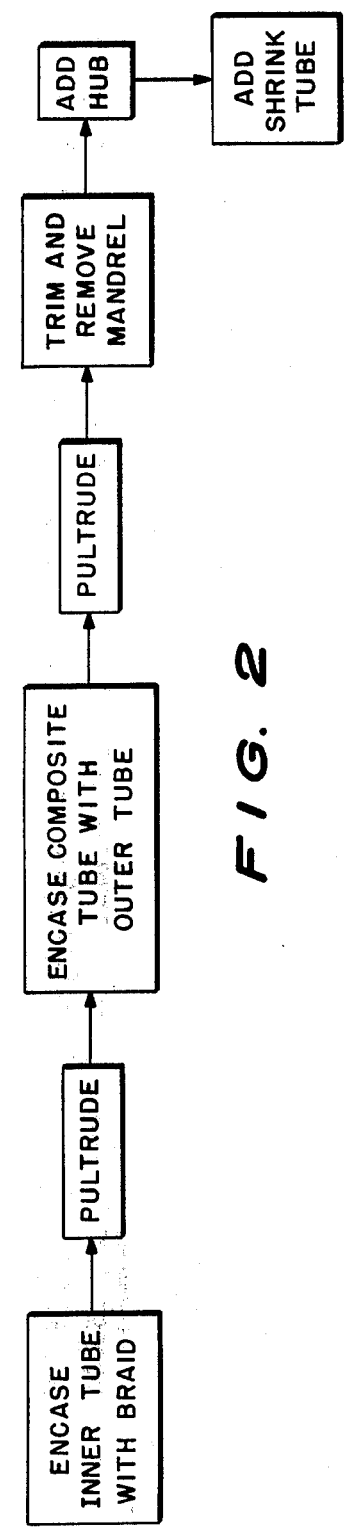
FIG. 2 is a flow diagram representing the steps employed in manufacturing the catheter illustrated in FIG. 1.
Figure 6:
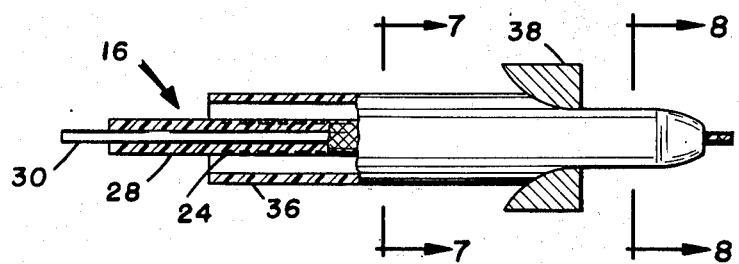
FIG. 6 is an illustration, partially in section, representing a later step in the inventive manufacturing procedure.
Figure 7:
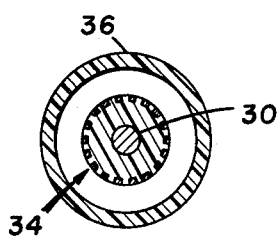
FIG. 7 is a cross section taken along line 7—7 of FIG. 6.

The next step in the manufacturing process, as seen in FIGS. 2, 6, and 7, is to cover the composite tube assembly 34 with an outer preformed thermoplastic tube 36. As shown in FIG. 6, the outer tube 36 completely covers the braid 24. However, the tube 36 does not extend to the distal tip 16, which, as will be recalled, is free from the braid 24.

Figure 8:
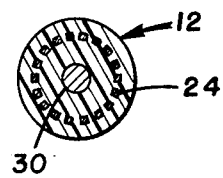
FIG. 8 is a cross section taken along line 8—8 of FIG. 6.

As the composite is pultruded, the outer tube 36 lengthens to completely cover the inner tube 28. Pultrusion occurs by pulling the structure shown in FIGS. 6 and 7 through a second heated die designated 38 in FIG. 6. Die 38 is typically heated to a temperature on the order of 220°C. The second heated die 38 ensures that the outer surface of the catheter main body 12 is of the desired diameter, and is smooth. As can be seen in FIG. 8, after being pulled through die 38, the non-metallic mesh 24 is totally entrained by what was once discrete inner and outer thermoplastic tubes and are also integral with the thermoplastic with which the braid is impregnated, and the inner and outer tubes become integral. There results a unified thermoplastic tube having a non-metallic mesh embedded therein.

The final stages in the manufacturing operation entail trimming off the proximal end 18 of main body 12 which was used as a griping site, the removal of the mandrel 30 from lumen 14, and the attachment of the knurled hub portion 20 and shrink tube 22.

The lumen 14 serves as the passage through which fluid is injected into the patient from a source connected to the catheter 10 at the proximal end thereof. The inner and outer diameters of tube 28 are chosen as a balance between the desired flow conditions through the catheter, and the control and flexure characteristics which must be attained. Susceptability to kinking and breaking are also to be considered. In this regard, an inner diameter of 0.052 inches and an outer diameter of 0.068 inches have been found suitable for the inner tube 28 of a 7 French catheter, commonly used in angiography. The inner tube 28 can be a medium or low density polyethylene with radiopacifying agent, in this manner protecting the lumen 14 from exposure to the braid 24, providing radiopacity, making the catheter 10 resistant to kinking, and improving torque control.

The braid sheath 24 is formed from a highly inelastic fibrous braid presaturated with thermoplastic, and wound into an essentially closed pattern. Any braid pattern, such as oppositely wound spirals or the like, may be employed. The material, configuration and dimensions of the braid 24 are selected to provide both the strength and flexibility necessary for the intended use. The braid layer provides torsional inelasticity and resistance to side wall rupture when the catheter is subjected to angiographic injection pressures. An example of a non-metallic braid sheath exhibiting the desired characteristics for a 7 French catheter would have an inner diameter of 0.068 inches, an outer diameter of 0.078 inches and be formed from carbon graphite or Kevlar 49. Other materials having a suitable Young's modulus (exceeding $5 \times 10^5$ p.s.i.) can be used. Several inches of the braid are removed from the distal tip 16 of the catheter 10 either by cutting, or by being folded back prior to the application of outer tube 36. In this manner, the distal tip of the catheter is free from the non-metallic braid, ensuring maximum flexibility at the leading end of the catheter. At the same time, the integral nature of the inner tube 28, ensures maximum strength and resistance to breakage, even at the distal end.

The outer tube 36 can be of the same general characteristics as those of the inner tube 28. For use as an angiographic catheter, a suitable inner diameter is 0.078 inches, and a suitable outer diameter is 0.092 inches.

An alternative method of applying outer tube 36 could be to flow coat inner tube composite 34 with a compatible plastic substance.

Figure 9A:
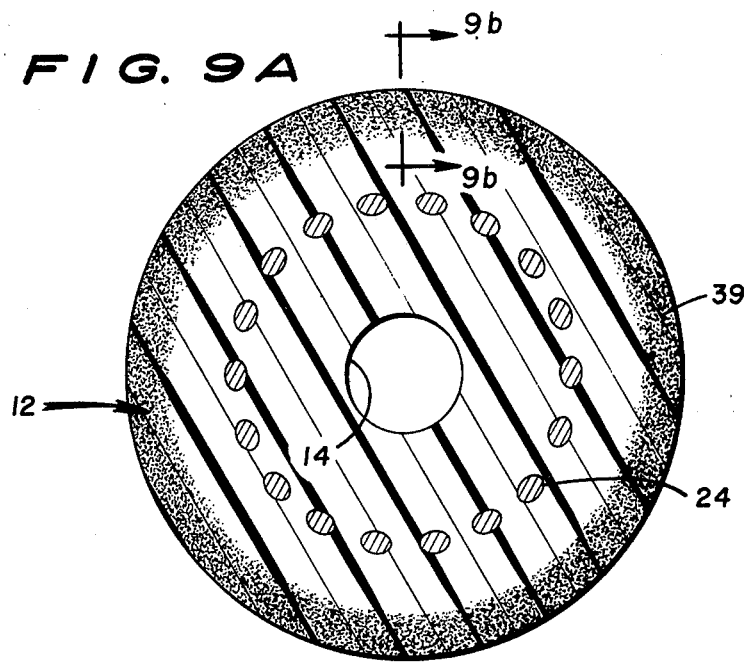
FIG. 9A is a cross section showing another embodiment of this inventive catheter.
Figure 9B:
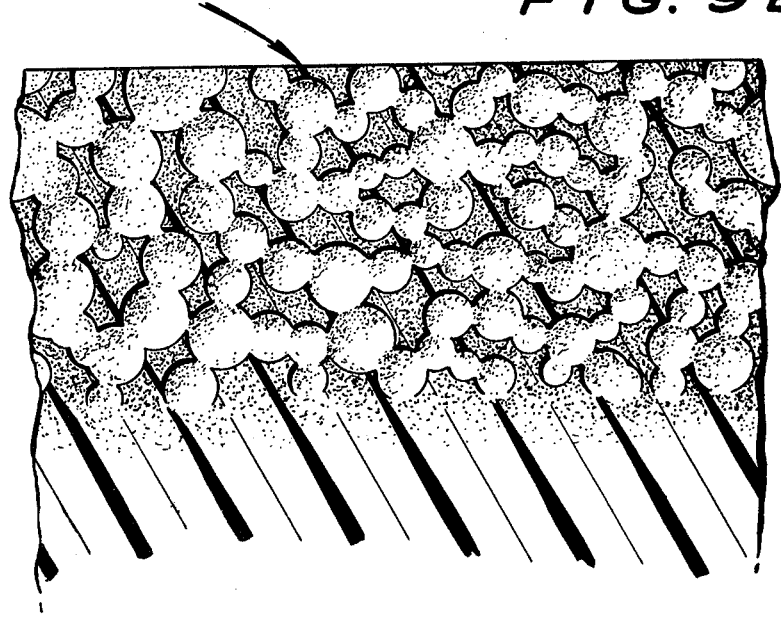
FIG. 9B is an enlarged detail of a portion of the catheter illustrated in FIG. 9A.

Another alternative illustrated in FIGS. 9A and 9B is where outer tube 36 is throughout or only on its outer surface a microporous open cell foamed plastic. Such a surface would be softer and less traumatic to blood vessel's intima and in addition could be a reservoir for an anticoagulant fluid such as a heparin solution or suspension. Such a solution or suspension could slowly leach from the catheter surface providing thromboresistance. The angiographer could infuse the solution into the plastic simply by pulling the catheter through a compression die located in an anti-coagulant solution. Air would be squeezed from the foamed plastic and the open cells would subsequently fill with anticoagulant solution. Such a catheter may have to be inserted into the body through an arteriotomy insertion sheath so as not to anticoagulate the arteriotomy site.

The technology of creating foamed plastics is well known and generally described on pages 146–153 of Modern Plastics Encyclopedia 74/75 Vol. 51, No. 10A. Specifically, outer tube 36 could be a plastic substance containing a physical foaming agent such as found on page 152 of the above reference. During the second pultrusion step, the volatile foaming agent would escape from the heated viscous plastic after leaving the heated die 38 resulting in a microporous surface 39.

Above, specific examples of the present invention have been described. It should be noted that these examples have been given for purposes of illustration only, and are in no way intended to limit the scope of the present invention. Rather, it is the intention that the present invention be limited only as defined in the appended claims.

We claim:

1. A method of manufacturing an elongated multiwall tube adapted for use as a catheter, the method comprising the steps of:

providing a first preformed elongated segment of flexible, tubular material;

encasing at least a portion of said first segment in a reinforcing braid sheath;

pulling said encased segment through a first heated die having an inside diameter less than the outside diameter of said encased segment to cause said segment to flow between the braids of said sheath to form a composite tube; and encasing said composite tube in a flexible material.

2. The method of claim 1, wherein said composite tube is encased in said flexible material by covering at least a portion of said composite tube with a second preformed elongated segment of flexible material and pulling said encased composite tube through a second heated die having an inside diameter less than the outside diameter of said encased composite tube, whereby said composite tube and said second segment are bonded together.

3. The method as defined in claim 2, wherein said second heated die is glass.

4. The method as defined in claim 1, wherein said braid sheath is terminated short of one end of said elongated multiwall tube.

5. The method as defined in claim 1, wherein said braid sheath is non-metallic.

6. The method as defined in claim 1, and further comprising the step of applying to said braid sheath a material compatible with said first segment for facilitating the development of said composite tube.

7. The method as defined in claim 1, and further comprising the steps of equipping one end of said elongated multiwall tube with a plurality of cylindrical segments, having different outside diameters and circumferences.

8. The method as defined in claim 7, wherein one of said cylindrical segments is a shrink tube fitted to the end of said multiwall tube by heating.

9. The method as defined in claim 7 wherein one of said cylindrical segments is a knurled handle portion.

10. The method of claim 1, wherein said first segment is of a thermoplastic material.

11. A catheter adapted for insertion and manipulation inside a patient's body, the catheter comprising:

an elongated continuous inner tube for conducting fluid flow;

an elongated braid sheath embedded and bonded to the surface of said inner tube, said braid sheath extending over a major portion of the length of said elongated inner tube;

an elongated outer tube covering at least a portion of said elongated inner tube and bonded thereto; said braid sheath having been embedded in said inner tube by covering said inner tube with said braid sheath and pulling the covered tube through a first heated die.

12. The catheter of claim 11, wherein said outer tube has been affixed to said inner tube with its embedded braid sheath, by covering said inner tube with said outer tube and pulling the covered inner tube through a second heated die.

13. The catheter of claim 11, wherein said braid sheath is impregnated with a material to facilitate bonding to said inner tube prior to associating with said first heated die.

14. The catheter of claim 11, wherein said braid sheath is non-metallic.

15. The catheter of claim 11, wherein said braid sheath comprises an essentially closed braid.

16. The catheter of claim 11, wherein said catheter is an angiographic catheter and said inner and outer tubes comprise radiopaque materials.

17. The catheter of claim 11, wherein said braid sheath comprises a non-metallic fibrous material having a Youngs modulus in excess of $5 \times 10^6$ p.s.i.

18. The catheter of claim 11, wherein said braid sheath is formed of carbon graphite.

19. The catheter of claim 11, wherein said braid sheath is formed of Kelvar 49.

20. The catheter of claim 11, wherein the distal tip of the catheter is integral with said inner tube.

21. The catheter of claim 11, wherein said outer tube is of a microporous material.

22. A multiwall elongated tube adapted for use as a catheter, the tube comprising:
- an elongated inner tube of flexible thermoplastic material having a proximal end and a distal end, and adapted to be inserted into a tortuous body passage such as a blood vessel;
- a reinforcing non-metallic substantially inelastic braid sheath saturated by said inner tube so that said braid sheath is embedded in the surface of said inner tube, said braid sheath extending substantially the entire length of said elongated inner tube; and
- an outer tube of a flexible thermoplastic material positioned over, coextensive with, and bonded to said inner tube.

23. The catheter of claim 22, wherein said braid sheath extends from said proximal end to a location spaced from the extreme distal end.

24. The catheter of claim 22, wherein said braid sheath is embedded in the surface of said inner tube by covering the inner tube with the braid sheath and pulling the same through a first heated die, and wherein said outer tube is bonded to the inner tube - braid sheath combination by covering the combination with the outer tube and pulling the same through a second heated die.

25. The catheter of claim 22, wherein said braid sheath extends from said proximal end to several inches from said distal end.

26. The catheter of claim 22, wherein said braid sheath is developed from at least two oppositely wound spirals.

27. The catheter of claim 21, wherein said braid sheath is impregnated with a material compatible with and to facilitate bonding to said inner and outer tubes.

28. A method of introducing a treating agent into the vascular system of an individual simultaneous with the introduction of a catheter into the vascular system, the method comprising the steps of:
- equipping the outside surface of a catheter with a porous material;
- temporarily impregnating the porous material with said treating agent; and
- introducing the impregnated catheter into the vascular system while said treating agent leeches out of said porous material.

29. The method of claim 28, wherein said treating agent is an anti-coagulant.

* * * * *